(12) United States Patent
Gundersen et al.

(10) Patent No.: US 8,351,040 B1
(45) Date of Patent: Jan. 8, 2013

(54) ELECTRIC GATED INTEGRATOR DETECTION METHOD AND DEVICE THEREOF

(76) Inventors: James Lowell Gundersen, Riverside, CA (US); James McChesney Hargrove, Riverside, CA (US)

(*) Notice: Subject to any disclaimer, the term of this patent is extended or adjusted under 35 U.S.C. 154(b) by 0 days.

(21) Appl. No.: 13/351,216

(22) Filed: Jan. 16, 2012

Related U.S. Application Data

(62) Division of application No. 12/434,685, filed on May 4, 2009, now Pat. No. 8,098,377.

(60) Provisional application No. 61/050,115, filed on May 2, 2008.

(51) Int. Cl.
*G01N 21/53* (2006.01)
(52) U.S. Cl. .... 356/437; 356/436; 356/432; 250/339.07
(58) Field of Classification Search .......... 356/432–440, 356/454, 484, 73; 250/339.07, 341.1, 343
See application file for complete search history.

(56) References Cited

U.S. PATENT DOCUMENTS

| | | | | |
|---|---|---|---|---|
| 5,528,040 A * | 6/1996 | Lehmann | | 250/343 |
| 6,233,052 B1 * | 5/2001 | Zare et al. | | 356/437 |
| 7,012,696 B2 * | 3/2006 | Orr et al. | | 356/454 |
| 7,277,177 B2 * | 10/2007 | Augustine et al. | | 356/437 |
| 7,301,639 B1 * | 11/2007 | Kebabian et al. | | 356/437 |
| 7,541,586 B2 * | 6/2009 | Miller | | 250/339.07 |
| 7,612,885 B2 * | 11/2009 | Cole et al. | | 356/437 |
| 2006/0232779 A1 * | 10/2006 | Shaw | | 356/436 |

* cited by examiner

*Primary Examiner* — Sang Nguyen
(74) *Attorney, Agent, or Firm* — Heidi L. Eisenhut; Loza & Loza, LLP

(57) ABSTRACT

A cavity ring down system is optimized to precisely measure trace gases or particles in an air sample by using time sampling detection and multiple-sample averaging resulting in a high signal-to-noise ratio. In one embodiment, a cavity ring down system is programmed to measure the rise time and the fall time of the light level in an optical cavity. The cavity ring down system is programmed to integrate a plurality of sample portions during a rise time and a plurality of sample portions during a fall time (in alternate intervals) to obtain a time constant with no sample present and a time constant with sample present. The measurements are used to calculate trace gases in the air sample.

7 Claims, 5 Drawing Sheets

Example Fall Time Measurement Interval

Example Rise Time Measurement Interval

ELECTRIC GATED INTEGRATOR DETECTION METHOD AND DEVICE THEREOF

CLAIM OF PRIORITY UNDER 35 U.S.C. §119

The present Utility Application for Patent claims priority to U.S. Provisional Application No. 61/050,115 entitled "Electric Gated Integrator Detection & Device Thereof" filed May 2, 2008, and hereby expressly incorporated by reference herein. May 2, 2009 falls on a Saturday, consequently the present application has been filed on Monday, May 4, 2009.

FIELD OF INVENTION

At least one feature pertains to the detection and measurement of trace chemical species or particles in gaseous samples.

BACKGROUND OF INVENTION

Air is a mixture of gases approximately composed of 78.08% nitrogen ($N_2$), 20.95% oxygen ($O_2$), 0.93% argon (Ar), 0.038% carbon dioxide ($CO_2$), trace amounts of other gases, and a variable amount (average around 1%) of water vapor. At ambient temperatures, the oxygen and nitrogen gases in air will not react with each other. However, in an internal combustion engine, combustion of a mixture of air and fuel produces combustion temperatures high enough to drive endothermic reactions between atmospheric nitrogen and oxygen in the flame, yielding various oxides of nitrogen, such as nitric oxide (NO) and nitrogen dioxide ($NO_2$). Mononitrogen oxides such as NO and $NO_2$ are typically referred to by the generic term $NO_x$.

Nitrogen dioxide ($NO_2$) is a major pollutant in the atmosphere of modern cities that is easily recognized by its reddish brown color. $NO_2$ is formed when nitric oxide (NO) is produced as a byproduct of combustion in internal combustion engines and power generators at temperatures greater than 800° C. and is oxidized by alkyl peroxy radicals in the atmosphere. In California and much of the United States, a principal source of NO is from trucks, since auto emissions have been successfully reduced by use of catalytic converters. $NO_2$ in the troposphere subsequently undergoes photolysis to ultimately form ozone ($O_3$) in the presence of sunlight. In the stratosphere, however, $NO_2$ is implicated in the destruction of $O_3$. Mixing ratios for $NO_2$ have been measured at sub-parts-per-billion levels in remote areas and up to hundreds of parts per billion (ppb) in urban areas.

Although techniques have been developed to measure atmospheric $NO_2$, these techniques have deficiencies related to interferences, stability and precision. As a result, the measured atmospheric $NO_2$ may not be accurate. Consequently, a technique to measure atmospheric NO and $NO_2$ that lacks interference and is more stable and precise is needed.

SUMMARY OF INVENTION

A method of measuring the presence of a gas in an air sample using a cavity ring down system, comprising: (i) collecting at least one current resulting from light introduced into an optical cavity when a light source is turned ON and while the air sample is being introduced into the optical cavity; (ii) measuring the at least one current resulting from light introduced into the optical cavity when a light source is turned ON; (iii) collecting at least one current resulting from light introduced into the optical cavity when the light source is turned OFF and while the air sample is being introduced into the optical cavity; and (iv) measuring the at least one current resulting from light introduced into the optical cavity when a light source is turned OFF is herein disclosed The method may further include: (i) collecting a plurality of additional currents resulting from light introduced into the optical cavity when a light source is turned ON; (ii) summing the plurality of additional currents resulting from light introduced into the optical cavity when a light source is turned ON to obtain a sample integrated rise time; (iii) collecting a plurality of additional currents resulting from light introduced into the optical cavity when a light source is turned OFF; and (iv) summing the plurality of additional currents resulting from light introduced into the optical cavity when a light source is turned OFF to obtain a sample integrated fall time. The collecting may be performed by a detector during a predetermined time period when the light source is ON or OFF.

The method may further include: (i) collecting at least one current resulting from light introduced into the optical cavity when a light source is ON and while no sample is being introduced into the optical cavity; (ii) measuring the at least one current resulting from light introduced into the optical cavity when a light source is ON; (iii) collecting at least one current resulting from light introduced into the optical cavity when the light source is OFF and while no sample is being introduced into an optical cavity; and (iv) measuring the at least one current resulting from light introduced into the optical cavity when a light source is OFF. The method may further include: (i) collecting a plurality of additional currents resulting from light introduced into the optical cavity when a light source is ON while no sample is being introduced; (ii) summing the plurality of additional currents resulting from light introduced into the optical cavity when a light source is ON while no sample is being introduced to obtain a reference integrated rise time; (iii) collecting a plurality of additional currents resulting from light introduced into the optical cavity when a light source is OFF while no sample is being introduced; and (iv) summing the plurality of additional currents resulting from light introduced into the optical cavity when a light source is OFF while no sample is being introduced to obtain a reference integrated fall time. The collecting may be performed by a detector during a predetermined time period when the light source is ON or OFF. The plurality of currents may be collected between 10,000 and 100,000 times. The method may further include using the reference integrated rise time, the reference integrated fall time, the sample integrated rise time and the sample integrated fall time to calculate an amount of absorbing gas present in the air sample wherein the amount of absorbing gas is represented by (i) the difference between reference integrated rise time and the sample integrated rise time and (ii) the difference between the reference integrated fall time and the sample integrated fall time. The light source may be a light-emitting diode or laser. The absorbing gas may be at least one of nitrogen dioxide, nitrogen trioxide, nitrous oxide, fluorine, chlorine, bromine, iodine, ozone, sulfur dioxide, chlorine dioxide, $HO_2$ radicals, OH radicals, formaldehyde, aldehydes, hydrocarbons, or an aromatic species. The combination of scattering and absorption by particles may be measured by the cavity ring down system.

A method of measuring the presence of a gas in an air sample using a cavity ring down system, including: when no sample is introduced into the system: (i) measuring an output voltage from a plurality of currents resulting from light introduced into an optical cavity when a light source is ON during a predetermined interval of a rise time of the light wherein the resulting measurement is a reference rise time measurement; (ii) measuring an output voltage from a plurality of currents resulting from light introduced into the optical cavity when the light source is OFF during a predetermined interval of a fall time of the light wherein the resulting measurement is a reference fall time measurement; (iii) measuring an output voltage from a plurality of currents resulting from light introduced into the optical cavity when a light source is ON during the rise time of the light wherein the resulting measurement is a reference steady state rise time measurement; and (iv) measuring an output voltage from a plurality of currents resulting from light introduced into the optical cavity when a light source is OFF during the fall time of the light wherein the resulting measurement is a reference steady state fall time measurement is herein disclosed.

The method may further include: when an air sample is introduced into the system: (i) measuring an output voltage from a plurality of currents resulting from light introduced into an optical cavity when a light source is ON during a predetermined interval of a rise time of the light wherein the resulting measurement is a sample rise time measurement; (ii) measuring an output voltage from a plurality of currents resulting from light introduced into the optical cavity when the light source is OFF during a predetermined interval of a fall time of the light wherein the resulting measurement is a sample fall time measurement; (iii) measuring an output voltage from a plurality of currents resulting from light introduced into the optical cavity when a light source is ON during the rise time of the light wherein the resulting measurement is a sample steady state rise time measurement; and (iv) measuring an output voltage from a plurality of currents resulting from light introduced into the optical cavity when a light source is OFF during the fall time of the light wherein the resulting measurement is a sample steady state fall time measurement.

The reference rise time measurement, the reference fall time measurement, the reference steady state rise time measurement, the reference steady state fall time measurement, the sample rise time measurement, the sample fall time measurement, the sample steady state rise time measurement and the sample steady state fall time measurement may be used to calculate the amount of gas in the air sample. Each output voltage may be collected between 10,000 and 100,000 times. The light source may be a light-emitting diode or laser. The absorbing gas may be at least one of nitrogen dioxide, nitrogen trioxide, nitrous oxide, fluorine, chlorine, bromine, iodine, ozone, sulfur dioxide, chlorine dioxide, $HO_2$ radicals, OH radicals, formaldehyde, aldehydes, hydrocarbons, or an aromatic species. The combination of absorption and scattering of particles may be measured by the cavity ring down system.

A method of measuring the presence of a gas in an air sample using a cavity ring down system, including at least one of: (a) collecting at least one current resulting from light introduced into an optical cavity when a light source is turned ON and while the air sample is being introduced into the optical cavity; and measuring the at least one current resulting from light introduced into the optical cavity when a light source is turned ON; or (b) collecting at least one current resulting from light introduced into the optical cavity when the light source is turned OFF and while the air sample is being introduced into the optical cavity; and measuring the at least one current resulting from light introduced into the optical cavity when a light source is turned OFF is herein disclosed. The measurements resulting from step (a) or step (b) may be used in combination with a total signal intensity to calculate the amount of gas in the air sample.

DETAILED DESCRIPTION

Figure 1:
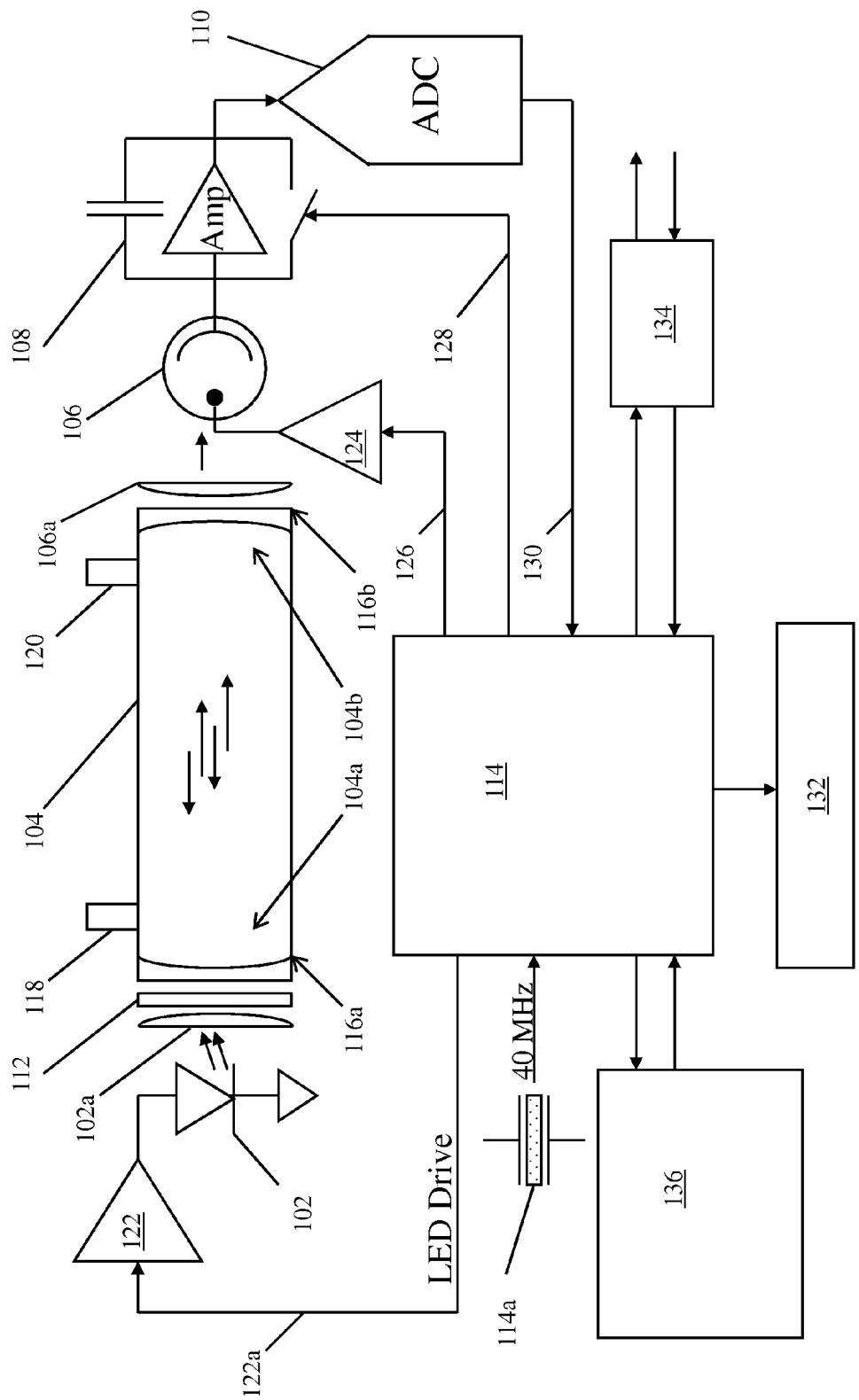
FIG. 1 illustrates a schematic of a cavity ring down system according to an embodiment of the invention.

The following detailed description is of the best currently contemplated modes of carrying out the invention. The description is not to be taken in a limiting sense, but is made merely for the purpose of illustrating the general principles of the invention.

One commonly used method of measuring atmospheric nitrogen dioxide ($NO_2$) is chemiluminescence in which conversion of $NO_2$ to nitric oxide (NO), either by catalytic thermal decomposition (which suffers from interferences from organic nitrates, HONO, $HNO_3$, etc.) or photolysis (which is relatively immune from interferences), is followed by reaction of NO with $O_3$ to produce electronically excited $NO_2^*$. The excited $NO_2^*$ emits a broad continuum radiation in the region of 500-900 nanometers (nm), with a signal strength that is proportional to the concentration of NO. Subtraction of the background NO concentration then yields the concentration of $NO_2$.

Chemiluminescence of nitric oxide (NO) by reaction with ozone is used extensively for quantifying NO and nitrogen dioxide ($NO_2$) in industrial smoke stack emissions, air quality monitoring stations and medical facilities, but suffers from quenching by water vapor and, at high enough concentrations, from $CO_2$, as well leading to erroneously low readings. An additional problem for $NO_2$ measurements using chemiluminescence is that catalytic thermal decomposition of $NO_2$ to NO for detection together as $NO_x$, where x=1 and/or 2, can lead to high $NO_2$ readings from other nitrogen-containing species, such as acyl peroxynitrates (PANs), alkyl nitrates and ammonia which all produce $NO_2$ upon thermal decomposition. This additional signal has resulted in $NO_x$-analyzers being termed $NO_y$-analyzers because they measure more than the sum of NO and $NO_2$. In the presence of quenching, the analyzers can actually indicate significantly less pollution as well. As a result, accurate measurements of $NO_2$ using the prior art approach of chemiluminescence cannot be reliably obtained.

In addition to the prior art approach of chemiluminescence, several $NO_2$ specific analyzers with low limits of detection have been demonstrated using techniques including cavity ring-down spectroscopy (CRDS) and its derivatives, continuous wave cavity ring-down (cw-CRDS), off-axis cw-CRDS, cavity attenuated phase shift spectroscopy (CAPS), and cavity enhanced absorption spectroscopy (CEAS). Tunable diode laser spectroscopy (TDLAS) and laser induced fluorescence (LIF) are more established techniques that measure $NO_2$ and could also be combined with chemiluminescence.

CRDS is a sensitive spectroscopy technique that is based on measurements of the rate of attenuation (k) rather than the magnitude of attenuation of the light by a sample. It can be used to measure the concentration of some light-absorbing substances, such as air pollutants. In CRDS, two ultra-high reflective mirrors face each other with a space (or cavity) in between. In the conventional pulsed laser implementation, a brief pulse of light is injected into the cavity and bounces (i.e., "rings") back and forth between the mirrors. Some small amount (typically around 0.1% or less) of the generated light enters and leaks out of the cavity and may be measured each time light hits one of the mirrors. As some light is lost (i.e., leaks out) on each reflection, the amount of light hitting the mirrors is slightly less each time. Furthermore, as a percentage leaks through, the amount of light measured also decreases with each reflection. If the only loss factor in the cavity is the reflectivity loss of the mirrors, one can show that the light intensity inside the cavity decays exponentially in time with a decay constant tau ($\tau$) (i.e., the "ring down time"). If a light-absorbing species is introduced into the cavity, the light will undergo fewer reflections before it disappears. In other words, CRDS measures the time it takes for the light to drop to a certain percentage of its original amount. The time change measured may be converted to a concentration.

As the absorption described above involves hundreds to thousands of passes of light through the sample, the sensitivity is greatly enhanced. CRDS is capable of measuring species of known absorption cross sections by taking the difference between the ring-down decay rate with sample ($1/\tau$) and the background decay rate without sample ($1/\tau_0$) and multiplying by $L/cl_s$:

$$\alpha = \frac{L}{cl_s}\left(\frac{1}{\tau} - \frac{1}{\tau_0}\right) = \sigma N \qquad \text{Equation 1}$$

where $\alpha$ is the absorption coefficient, c is speed of light, L is the cavity length, and $l_s$ is the sample path length. The resulting absorption coefficient, $\alpha$, can then be divided by the known cross section of the sample, or sigma ($\sigma$), to yield the concentration or number density (N).

In some prior art arrangements, phase shift measurements have relied on the use of quadrature lock-in amplifiers which are not sufficiently accurate at the modulation frequencies encountered in this type of device to provide high phase resolution. In other prior art arrangements, a frequency divider chain starting from a single clock and generating both in-phase and quadrature reference signals is used.

Additionally, prior art pertaining to detection of signal time decay relies on high-speed sampling of the decaying signal followed by conversion to a digital signal. This technique requires the use of an expensive combination of a laser, a photomultiplier, high-speed sampling and digitizing circuitry. In other prior art pertaining to detection of signal time decay, each modulation cycle of the light source is divided into a finite number of equal consecutive windows followed by integration of the light signal recorded during each of those windows. These windows may be generated by division from a single frequency source. Both methods suffer from deficiencies with respect to precision, cost and robustness of the method.

According to embodiments of the invention, a cavity ring down system can be optimized to precisely measure trace gases in an air sample by using time sampling detection and multiple-sample averaging resulting in a high signal-to-noise ratio. In one embodiment, a cavity ring down system is programmed to measure the rise time and the fall time of the light level in an optical cavity. These values are combined to form a ratio (see Equation 2) that can be used to find the decay time constant (see Equation 3). More specifically, the cavity ring down system is programmed to integrate a plurality of sample portions during a rise time and a plurality of sample portions during a fall time (in alternate intervals). In one implementation, a series of rise time data and a series of fall time data are collected in alternate intervals. Each integrated series gives an indication of the characteristic time constant ($\tau_0$) of the cavity that is used to generate a reference time constant (see Equation 1). When the rise time measurement and fall time measurement (or successive pairs of measurements) are added (i.e., rise time plus fall time), the sum represents the full-scale signal and provides an indication of the intensity of the light source that is needed to most accurately calculate the time constant ($\tau_0$) (see Equation 1). Additionally, the absolute difference (i.e., rise time minus fall time) between the rise time measurement and the fall time measurement can also be calculated and divided by the sum (full-scale signal). When the ratio, i.e., (the rise time minus the fall time) is divided by (the rise time plus the fall time), represented by the formula:

$$\text{Ratio} = \frac{\text{rise time} - \text{fall time}}{\text{rise time} + \text{fall time}} \qquad \text{Equation 2}$$

this Ratio along with the period (P), the start time of sampling ($t_1$) and the end time of sampling ($t_2$) can be input into the following equation to reiteratively solve for the decay time constant ($\tau$):

$$\text{Ratio} = 1 + 2\left(1 - \frac{e^{(-P/2\tau)}}{1 + e^{(-P/2\tau)}}\right)\frac{\tau}{(t_2 - t_1)}(e^{(-t_2/\tau)} - e^{(-t_1/\tau)}) \qquad \text{Equation 3}$$

The decay time constant ($\tau$) is assumed to be the same for the rise time. The decay time constant ($\tau$) is used to calculate the decay rate (k) as the inverse of the decay time constant ($\tau$) by the following equation:

$$\text{Rate} = k\frac{1}{\tau} \qquad \text{Equation 4}$$

$$\alpha = \frac{1}{c}(k - k_0) \qquad \text{Equation 5}$$

where c is the speed of light, k is the rate obtained in Equation 3 (with sample) and $k_0$ is the rate obtained when the cell is empty (no sample). The absorption coefficient can then be used to calculate the number density (N) by the following formula:

$$N = \frac{\alpha}{\sigma} \qquad \text{Equation 6}$$

where N is the number density and $\sigma$ is the cross section of the absorbing or scattering species. The concentration in parts per million or parts per billion may be obtained by dividing the number density by the total number density ($N_T$) corrected for pressure (P) and temperature (T) where k is the Boltzmann constant.

$$N_T = \frac{P}{kT} \qquad \text{Equation 7}$$

$$\text{Concentration}(ppb) = \frac{N}{N_T} \times 10^{-9} \qquad \text{Equation 8}$$

In an alternative embodiment, a cavity ring down system is programmed to measure the total signal intensity ($I_o$) and one of the rise time or fall time to obtain a rate equation which can be used to solve for the rate of the sample (or no sample) (see Equation 4; Equations 5-8). More particularly, $I_o$ may be obtained by taking a measurement while the light source is ON and taking a measurement while the light source is OFF The difference between these two measurements is $I_o$. These measurements are taken after the decay and rise of light in the light cavity occur whereas the rise and fall times are taken immediately after the light is turned on or off. Either the integrated decay rate or the integrated rise rate can then be divided by $I_o$ to obtain the rate equation which can subsequently be used to obtain a rate equation which can be used to solve for the rate of the sample (or no sample). Either the decay rate or the rise rate can be calculated independently from the following equations:

$$\int_{t_1}^{t_2} Sdt = I_o(e^{-kt_2} - e^{-kt_1}) \qquad \text{Equation 8}$$

$$\int_{t_1}^{t_2} Sdt = I_o(t_2 - t_1 - e^{-kt_2} + e^{-kt_1}) \qquad \text{Equation 9}$$

FIG. 1 illustrates a schematic of a CRDS according to an embodiment of the invention. Principle components of CRDS 100 generally include (upstream to downstream) a light source 102, an optical cavity 104, a detector 106, an integrator 108 and a converter 110. Light source 102 with the aid of an associated lens or lenses 102a may be directed toward a proximal end 104a of optical cavity 104 while a distal end 104b of optical cavity 104 may be directed toward detector 106 with the aid of an associated lens 106a. In one embodiment, a bandpass filter 112 is positioned between light source 102 and proximal end 104a of optical cavity 104. In an alternative embodiment, bandpass filter 112 is positioned between distal end 104b of optical cavity 104 and detector 106. Detector 106 may be in electrical communication with integrator 108, and integrator 108 may be in electrical communication with converter 110. All components (i.e., light source 102, optical cavity 104, detector 106, integrator 108 and converter 110) may be controlled and/or driven by a computer 114. A quartz crystal oscillator 114a provides a stable and accurate timing source for computer 114 instruction stepping and timing and, in turn, for the integration measurement interval (explained in more detail below).

In one embodiment, light source 102 may be a non-coherent light source such as a light-emitting diode (LED). Other examples of light sources include, but are not limited to, a laser, a blackbody radiator, a flashlamp discharge or other gas discharge. In embodiments in which light source 102 is an LED, the LED color and bandpass filter color are selected to provide light in a preferred narrow spectral bandwidth, for example, between about four-hundred and two (402) nanometers to about four-hundred and twelve (412) nanometers.

In one embodiment, optical cavity 104 may include two highly reflective plano/concave mirrors 116a and 116b situated internally at each end therein (i.e., at proximal end 104a and distal end 104b of optical cavity 104). Each mirror 116a, 116b may have a diameter of approximately one inch (2.54 centimeters). In some embodiments, optical cavity 104 may have a cylindrical shape and may be, for example, between about 0.25 inches (0.635 centimeters) to about 1.50 inches (3.81 centimeters) in diameter, preferably about one inch (2.54 centimeters) in diameter, i.e., approximately close to the effective diameter of each mirror 116a, 116b. The distance between mirrors 116a and 116b may be, for example, between about five (5) inches (12.7 centimeters) and about fifty (50) inches (127 centimeters). According to one embodiment, a sample inlet 118 is in fluid communication with (or coupled to) optical cavity 104, and, similarly, a pump inlet 120 is also in fluid communication with (or coupled to) optical cavity 104. During operation of CRDS 100, a sample may be introduced into optical cavity 104 via sample inlet 118 and removed from optical cavity 104 via pump inlet 120.

In one embodiment, detector 106 with the aid of lens 106a (i.e., proximate to distal end 104b of optical cavity 104) functions to collect photons emitting from optical cavity 104 continuously or during predetermined time intervals (explained in more detail below). Detector 104 may be, for example, a phototube (PT), a photomultiplier tube (PMT), or an avalanche photodiode (APD). Integrator 108 (in electrical communication with detector 106) collects a current sample from detector 106 while converter 110 (in electrical communication with integrator 108) measures output voltage from integrator 108.

According to one method, computer 114 drives light source 102 (arrow 122a), e.g., LED 102, via an amplified buffer 122 by generating a square wave input current which results in LED 102 being repeatedly turned ON and OFF. The amplified buffer 122 may use a constant current source to stabilize the output light level of the LED 102. The period of the resultant modulated current is chosen to be approximately $1/(4*\tau)$ where $\tau$ is a time in microseconds. For example, if $\tau$ is two (2) microseconds, then the LED drive period would be eight (8) microseconds and the frequency would be nominally one-hundred and twenty-five (125) kilohertz (KHz). In another example, if $\tau$ is twenty (20) microseconds, then the LED drive period would be eighty (80) microseconds and the frequency would be nominally twelve and one-half (12.5) KHz. Pulsed light emanating from LED 102 then illuminates optical cavity 104. The light level in optical cavity 104 builds up, i.e., rises, while LED 102 is ON and then decays, i.e., falls, while LED 102 is OFF.

The light escaping from distal end 104b of optical cavity 104 is focused on to detector 106 with the aid of lens 106a which in turn converts the photons from the light into electrons. Detector 106 collects the photons emitted from optical cavity 104 only when gated (i.e., driven ON by an amplified buffer 124). There are two separate measurements made, one during the "ring up" or rise time portion of the resonant cavity cycle (LED 102 ON) and the other during the "ring down" or fall time portion of the resonant cavity cycle (LED 102 OFF). The sample time signal output (arrow 126) from computer 114 to detector 106 defines this gated detection time (see FIGS. 2-3). This process gives a small current sample which is collected in integrator 108. This process is repeated over, for example, ten-thousand to one hundred thousand sample readings (i.e., for about 0.1 to 1 second) which in turn creates a significant output voltage at integrator 108 (see FIGS. 4-5). The output voltage is then measured by converter 110, which may be, for example, a high-resolution analog-to-digital converter. After the end of the previous measurement cycle and before the beginning of the next measurement cycle, the integrator 108 may be reset (arrow 128) by computer 114 and the initial output voltage of integrator 108 may be measured by converter 110, i.e., the initial output voltage of integrator 108 is measured between cycles. Measuring the initial output voltage of the integrator is more accurate than assuming the reset output voltage is "zero". The difference between the final output voltage and the initial output voltage, e.g., the Rise Voltage of FIG. 4 is the measure of charge (photons) collected during the sampling of the "rise" time over the measurement interval. This process is repeated for the "fall time" or "ring down" portion of the resonant cavity cycle, i.e., when LED 102 is OFF (see FIG. 5). The "rise" time signal or ring-up (i.e., photons captured when LED 102 is ON) and the "fall" time signal or ring-down (i.e., photons captured when LED 102 is OFF) are consequently measured and may be used to calculate a ratio, more particularly, the ratio of the difference between the rise time and the fall time (i.e., rise time minus fall time) divided by the sum of the rise time and the fall time (i.e., rise time plus fall time), represented by the following formula:

$$\text{Ratio} = \frac{\text{rise time} - \text{fall time}}{\text{rise time} + \text{fall time}} \quad \text{Equation 2}$$

This ratio may be used to calculate the decay rate (k) represented by Equation 2. This ratio may also be the average of many measurements.

After measurement of the output voltage of the integrator 110, computer 114 receives the given measurement (arrow 130) and generates a reading. Such reading may be used to calculate the decay time constant ($\tau_0$) of an empty optical cavity 104 and changes in the decay time ($\tau$) caused by addition of an absorbing gas or scattering particles to the gas sample. The decay time constant ($\tau_0$) of an empty optical cavity 104 and changes in the decay time ($\tau$) are then used as a reference to calculate concentration of an absorbing gas (explained in more detail below). The concentration of the absorbing gas may be displayed on user interface 132 or sent to an external computer before or after processing using the external data link (arrow 134). Computer 114 also serves as the regulator and/or controller for the various functions while the CRDS 100 is in operation. For example, computer 114, which in some embodiments may be a single microchip, controls the square-wave drive of the light source 102 (arrow 102*a*), the sampling width, position and the interval of the measurement time (arrow 126) of detector 106, and resetting (arrow 128) of the integrator 108. Computer 114 may also serve to measure and control the environment (box 136), i.e., computer 114 can measure the atmospheric pressure and temperatures within the unit, and/or, stabilize the temperature of optical cavity 104 and electronics (i.e., making the quartz crystal oscillator 114*a* more stable) by controlling heaters to keep the temperature constant. Computer 114 may also serve to calculate the mathematical algorithms necessary to correlate the readings with the quantity of gas detected and/or measured.

Figure 2:
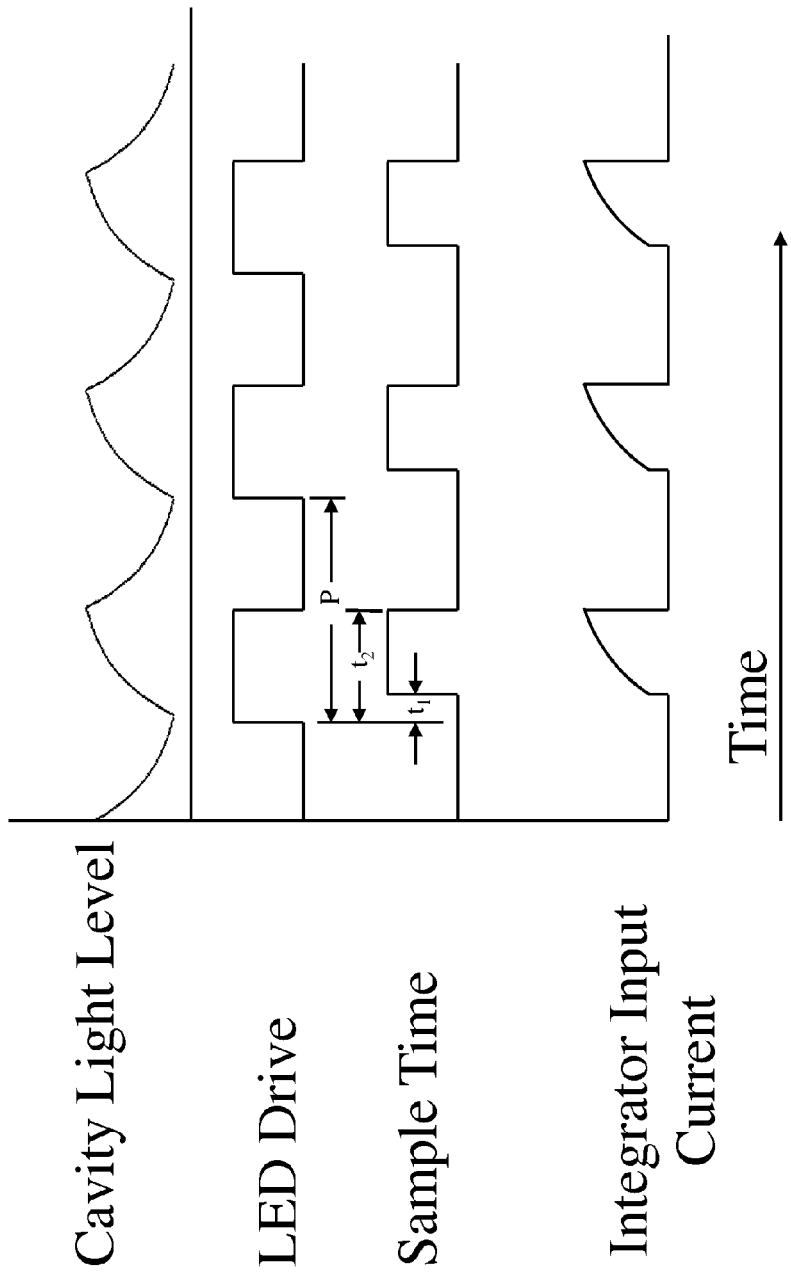
FIG. 2 is a graphical representation of a "rise" time signal measurement generated from a CRDS during a predetermined time period.

FIG. 2 is a graphical representation of a "rise" time signal measurement generated from a CRDS during a predetermined time period. FIG. 2 illustrates the sample time signal in relation to the cavity light level, the LED drive and the integrator input (i.e., the gated photon generated current from the detector). More particularly, FIG. 2 illustrates the cavity light level as a function of the LED being turned ON and OFF. Referring to the LED Drive, the crest of the square wave represents when the LED is ON while the valley of the square wave represents when the LED is OFF. For the "rise" time signal measurement, a sample reading is taken during the time period when the LED is ON, i.e., the "ring up" or rise time.

Figure 3:
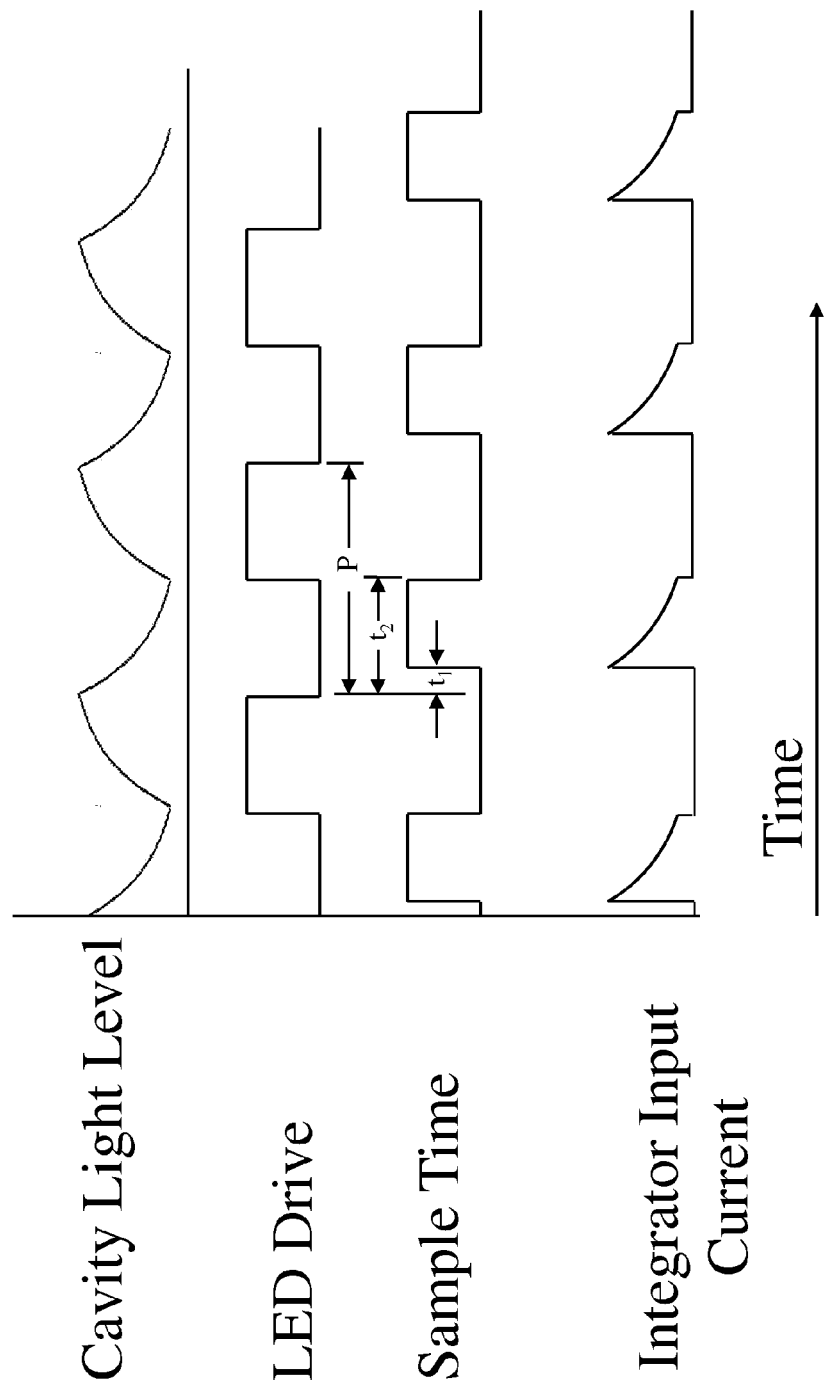
FIG. 3 is a graphical representation of a "fall" time signal measurement generated from a CRDS during a predetermined time period.
Figure 4:
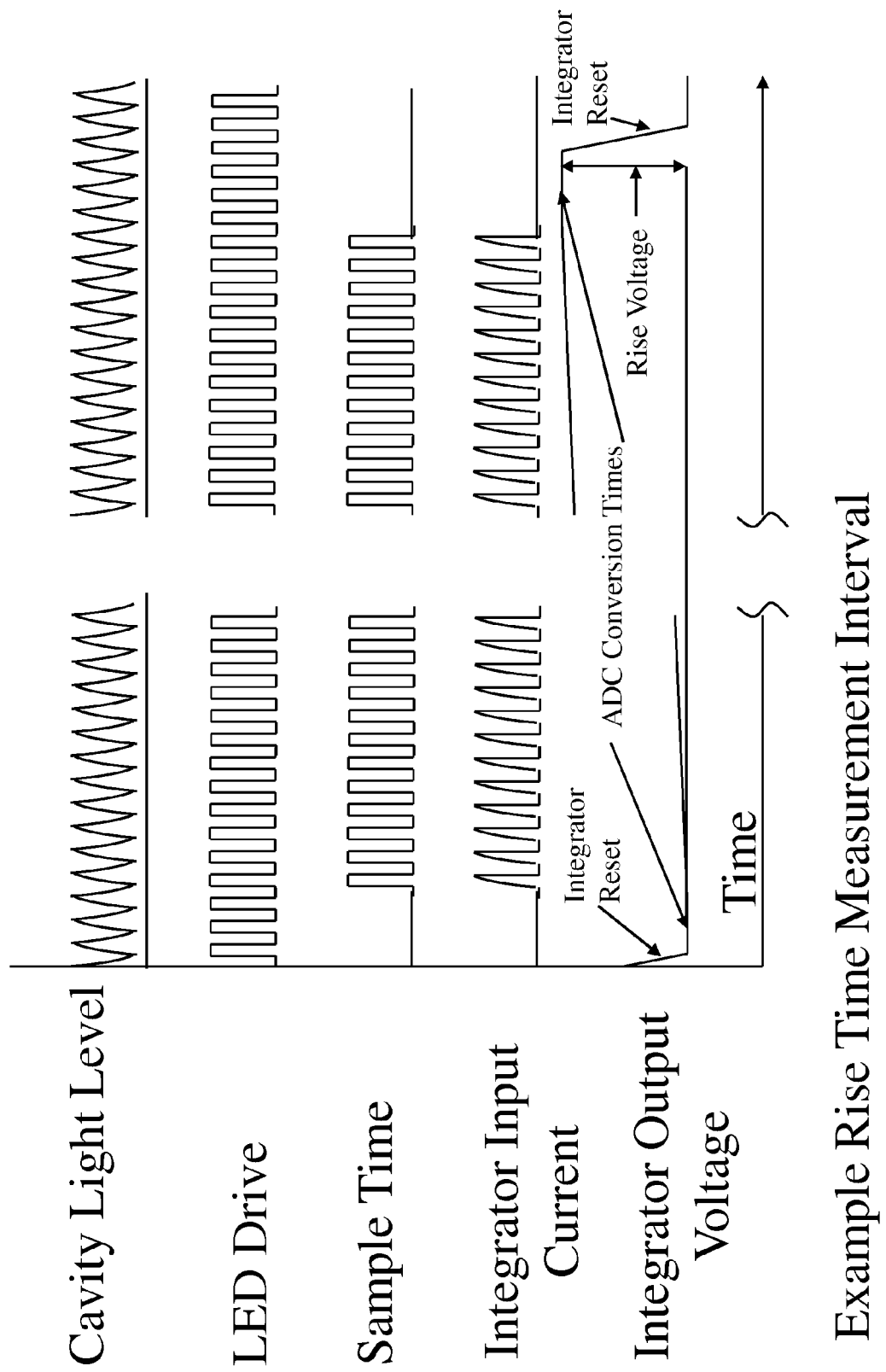
FIG. 4 is a graphical representation of an example rise time measurement interval.

FIG. 3 is a graphical representation of a "fall" time signal measurement generated from a CRDS during a predetermined time period. FIG. 3 illustrates the sample time signal in relation to the cavity light level, the LED drive and the integrator input (i.e., the gated photon generated current from the detector). More particularly, FIG. 3 illustrates the cavity light level as a function of the LED being turned ON and OFF. Referring to the LED Drive, the crest of the square wave represents when the LED is ON while the valley of the square wave represents when the LED is OFF. For the "fall" time signal measurement, a sample reading is taken during the time period when the LED is OFF, i.e., the "ring down" or fall time.

FIG. 4 is a graphical representation of an example rise time measurement interval. It depicts a time interval of between 0.1 and 1.0 seconds. It shows the resultant integrator output voltage, or "rise" voltage, which is the measurement of the rise time signal component. It also shows an example of the integrator reset time and the ADC conversion times just before the start of integration and just after the completion of the integration.

Figure 5:
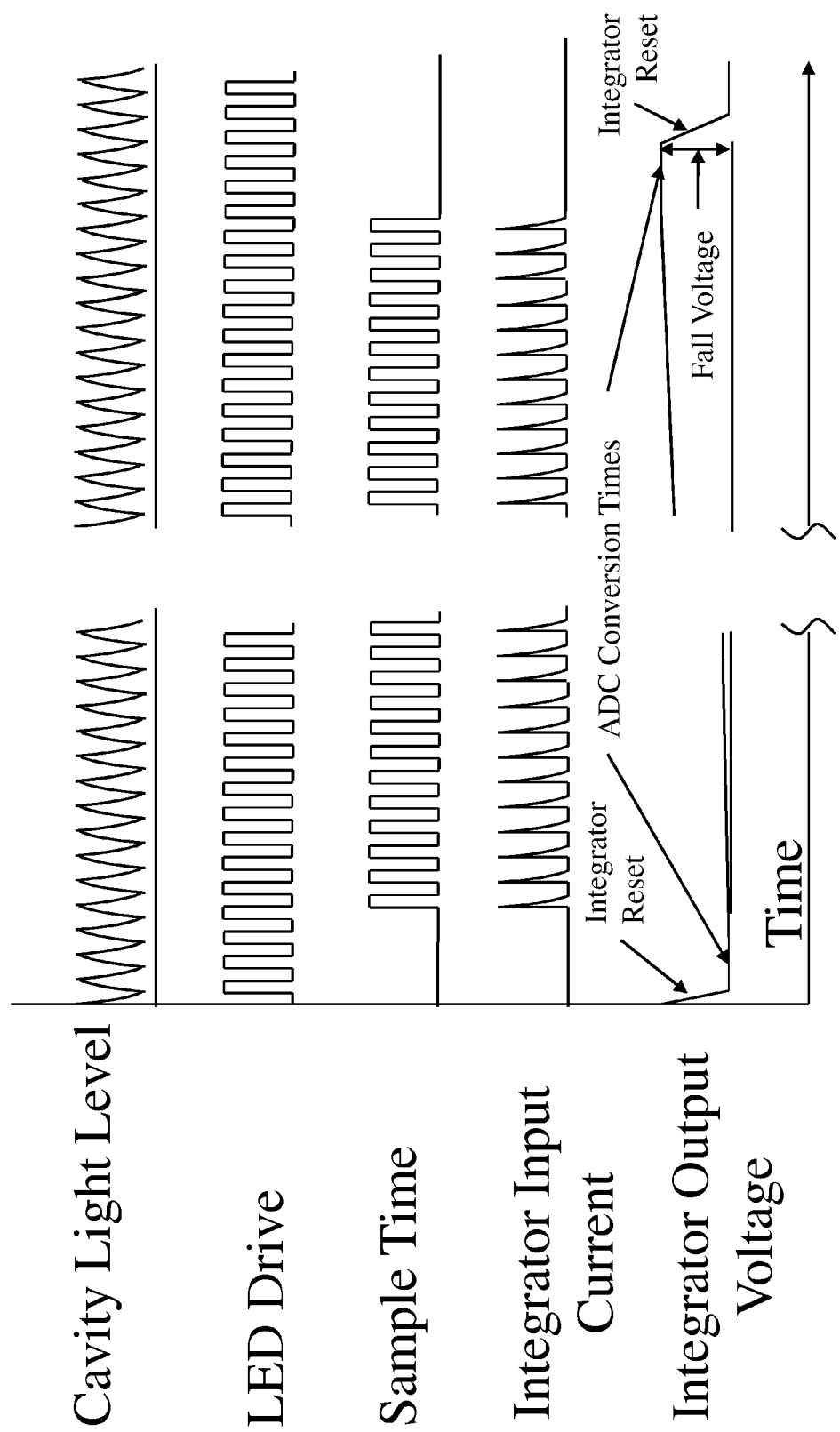
FIG. 5 is a graphical representation of an example fall time measurement interval.

FIG. 5 is a graphical representation of an example fall time measurement interval. It depicts a time interval of between 0.1 and 1.0 seconds. It shows the resultant integrator output voltage, or "fall" voltage, which is the measurement of the fall time signal component. It also shows an example of the integrator reset time and the ADC conversion times just before the start of integration and just after the completion of the integration. The "fall" voltage represented in FIG. 5 is less than the corresponding "rise" voltage represented in FIG. 4.

The addition of an absorbing gas (such as certain gases found in polluted air) causes the rise and fall times to decrease. These changes in the rise and fall times can be detected and measured and then used to calculate the amount of an absorbing gas present by comparison with the "no sample" reference data (explained previously). Thus, according to an embodiment of a method of the invention, the above process may be performed while a sample is introduced via sample inlet 118 and pumped out via pump outlet 120 to obtain data correlating to the introduced sample. In one embodiment, the sample may be introduced continuously. The CRDS 100 may detect absorbing species in gas samples with any particles present filtered out or, alternatively, CRDS 100 may detect particles if any absorbing gases such as $NO_2$ are removed, i.e., filtered out. Examples of absorbing gases that may be measured and quantified according to embodiments of the invention include, but are not limited to, nitrogen dioxide, nitrogen trioxide, fluorine, chlorine, bromine, iodine, ozone, sulfur dioxide, chlorine dioxide, $HO_2$ radicals, hydroxy radicals, and hydrocarbons, including aldehydes and aromatic species.

In contrast to prior art methods which look at decay rate only, the methods according to embodiments of the invention take into account both the rise and fall rates of the light emitted from a light source to generate a more precise reading of absorbing gases within a sample. Such method may be referred to as "time domain sampling." A key element to time domain sampling is the gated light detection performed by the detector, which allows photons to be detected and integrated without including wide bandwidth electronic noise associated with narrow time domain samples. Assuming photon noise dominates, the precision of a measurement may be doubled by increasing the integration time by a factor of four in view of that the photon noise level is the square root of the number of photons collected.

Representatively, a sample of 1000 collected photons results in a noise level of 3%, i.e., the square root of 1000 is approximately 30 which is then divided by 1000. On the other hand, a sample of 1,000,000 collected photons results in a noise level of 0.01%, i.e., the square root of 1,000,000 equals 1000 which is then divided by 1,000,000. Thus, according to an embodiment of the invention, integration of many samples gives a high photon count with a low noise, i.e., low signal to noise ratio, resulting in better precision and stability.

Advantageously, embodiments of devices and methods of the invention lend itself to higher precision stability via the more precise reference measurements (explained previously), temperature control, atmospheric pressure measurement, and a minimum number of analog and digital parts, e.g., low noise operational amplifier, a stable integrating capacitor, a high resolution delta-sigma ADC, the LED and the phototube. Moreover, embodiments of devices and methods of the invention lend itself to a minimum cost and minimum number of components for its performance capability. For example, buffers to drive the LED and the phototube, an integrator (an op amp, summing capacitor, and reset circuitry), a high resolution ADC, a display (an LCD driver and LCD) and an external interface can be controlled by a single chip microcontroller. Furthermore, embodiments of devices of the invention are flexible because many variables are controlled by the software, e.g., the cycle period, the LED ON and OFF time, the sample time, the reset time and the integration time. This lends itself to easy adjustability to, for example, changes in the optical cavity's length or mirror reflection coefficients can be accommodated by simply changing the measurement timing through changes in the software when needed. In some embodiments, the software can automatically optimize measurements.

While certain exemplary embodiments have been described and shown in the accompanying drawings, it is to be understood that such embodiments are merely illustrative of and not restrictive on the broad invention, and that this invention is not be limited to the specific constructions and arrangements shown and described, since various other modifications may occur to those ordinarily skilled in the art.

What is claimed is:

1. A method of measuring the presence of a gas in an air sample using a cavity ring down system, comprising:
when no sample is introduced into the system:
measuring an output voltage from a plurality of currents resulting from light introduced into an optical cavity when a light source is ON during a predetermined interval of a rise time of the light wherein the resulting measurement is a reference rise time measurement;
measuring an output voltage from a plurality of currents resulting from light introduced into the optical cavity when the light source is OFF during a predetermined interval of a fall time of the light wherein the resulting measurement is a reference fall time measurement;
measuring an output voltage from a plurality of currents resulting from light introduced into the optical cavity when a light source is ON during the rise time of the light wherein the resulting measurement is a reference steady state rise time measurement; and
measuring an output voltage from a plurality of currents resulting from light introduced into the optical cavity when a light source is OFF during the fall time of the light wherein the resulting measurement is a reference steady state fall time measurement;
wherein the reference rise time measurement, the reference fall time measurement, the reference steady state rise time measurement, and the reference steady state fall time measurement are used to calculate the amount of gas in the air sample by a computer.

2. The method of claim 1, further comprising:
when an air sample is introduced into the system:
measuring an output voltage from a plurality of currents resulting from light introduced into an optical cavity when a light source is ON during a predetermined interval of a rise time of the light wherein the resulting measurement is a sample rise time measurement;
measuring an output voltage from a plurality of currents resulting from light introduced into the optical cavity when the light source is OFF during a predetermined interval of a fall time of the light wherein the resulting measurement is a sample fall time measurement;
measuring an output voltage from a plurality of currents resulting from light introduced into the optical cavity when a light source is ON during the rise time of the light wherein the resulting measurement is a sample steady state rise time measurement; and
measuring an output voltage from a plurality of currents resulting from light introduced into the optical cavity when a light source is OFF during the fall time of the light wherein the resulting measurement is a sample steady state fall time measurement.

3. The method of claim 2, wherein the calculated amount of gas in the air sample is refined by including, the sample fall time measurement, the sample steady state rise time measurement and the sample steady state fall time measurement.

4. The method of claim 3 wherein each output voltage is collected between 10,000 and 100,000 times.

5. The method of claim 1 wherein the light source is a light-emitting diode or laser.

6. The method of claim 1 wherein the absorbing gas is at least one of nitrogen dioxide, nitrogen trioxide, nitrous oxide, fluorine, chlorine, bromine, iodine, ozone, sulfur dioxide, chlorine dioxide, $HO_2$ radicals, OH radicals, formaldehyde, aldehydes, hydrocarbons, or an aromatic species.

7. The method of claim 1 wherein the combination of absorption and scattering of particles is measured by the cavity ring down system.

* * * * *